United States Patent
Shen et al.

(10) Patent No.: US 9,495,772 B2
(45) Date of Patent: Nov. 15, 2016

(54) CT IMAGING SYSTEMS AND METHODS THEREOF

(71) Applicants: NUCTECH COMPANY LIMITED, Beijing (CN); TSINGHUA UNIVERSITY, Beijing (CN)

(72) Inventors: Le Shen, Beijing (CN); Yuxiang Xing, Beijing (CN); Yuanji Li, Beijing (CN); Chuqing Feng, Beijing (CN); Li Zhang, Beijing (CN); Zhiqiang Chen, Beijing (CN)

(73) Assignees: NUCTECH COMPANY LIMITED, Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 14/758,795

(22) PCT Filed: Oct. 31, 2013

(86) PCT No.: PCT/CN2013/086287
§ 371 (c)(1),
(2) Date: Jun. 30, 2015

(87) PCT Pub. No.: WO2014/101567
PCT Pub. Date: Jul. 3, 2014

(65) Prior Publication Data
US 2015/0356755 A1 Dec. 10, 2015

(30) Foreign Application Priority Data
Dec. 31, 2012 (CN) .......................... 2012 1 0593047

(51) Int. Cl.
*A61B 6/00* (2006.01)
*G06T 11/00* (2006.01)
*G06T 5/50* (2006.01)
*G01N 23/04* (2006.01)
*G01T 1/29* (2006.01)
*A61B 6/03* (2006.01)

(52) U.S. Cl.
CPC ............ *G06T 11/005* (2013.01); *A61B 6/032* (2013.01); *A61B 6/4241* (2013.01); *A61B 6/4266* (2013.01); *A61B 6/482* (2013.01); *A61B 6/5205* (2013.01); *G01N 23/046* (2013.01); *G01T 1/2985* (2013.01); *G06T 5/50* (2013.01); *G01N 2223/419* (2013.01); *G06T 2207/10081* (2013.01); *G06T 2207/20182* (2013.01)

(58) Field of Classification Search
USPC ........................................................ 378/1, 4
See application file for complete search history.

(56) References Cited

U.S. PATENT DOCUMENTS

| | | | |
|---|---|---|---|
| 6,990,171 | B2 | 1/2006 | Toth et al. |
| 2008/0277591 | A1 | 11/2008 | Shahar et al. |

FOREIGN PATENT DOCUMENTS

| | | |
|---|---|---|
| CN | 101405619 A | 4/2009 |
| CN | 102076263 A | 5/2011 |
| CN | 102106740 A | 6/2011 |
| CN | 102448376 A | 5/2012 |
| JP | 2012-034901 A | 2/2012 |
| WO | WO 2012/009725 A1 | 1/2012 |

*Primary Examiner* — Nicole Ippolito
*Assistant Examiner* — Hanway Chang
(74) *Attorney, Agent, or Firm* — Baker & Hostetler LLP

(57) ABSTRACT

CT imaging systems and methods thereof are disclosed. A common CT scanning is performed on an object to obtain a common CT imaging. An area of interest is determined from the image. A CT scanning is performed on the area of interest under a plurality of energy windows by a photon counter detector. A high resolution image of the area of interest is reconstructed. The discrimination of energy spectrum is higher and the result so obtained is more stable by using a photon counter detector to collect photon count projection data of a plurality of energy windows and thus it may be decomposed into a plurality of basis functions.

18 Claims, 4 Drawing Sheets

CT IMAGING SYSTEMS AND METHODS THEREOF

CROSS-REFERENCE TO RELATED APPLICATIONS

This application is the National Stage of International Application No. PCT/CN2013/086287, filed on Oct. 31, 2013, entitled "CT IMAGING SYSTEM AND METHOD," which claims priority to Chinese Patent Application No. 201210593047.4 filed on Dec. 13, 2012, the disclosures of which are incorporated herein by reference in their entireties.

TECHNICAL FIELD

The present embodiments generally relate to radiation imaging technique, and more particularly, to a CT imaging system and method thereof.

BACKGROUND

The conventional single-energy or dual-energy X ray imaging techniques usually use a scintillator-type detector, and signals thus collected reflect a total energy deposition of X rays of multiple colors. An energy deposition is an energy weighted integral of X-ray energy spectrum. Therefore, the imaging result cannot reveal energy attenuation information of a material under certain energy.

The dual-energy imaging technique comprises CTs of multiple energies, and utilizes different X-ray energy spectrum to perform imaging, and thus may discriminate materials to a certain extent. However, the imaging result has a system error due to the limitation caused by the physical model. Furthermore, there must be an overlapping area between the X-ray energy spectrum, which may affect the capability of discriminating materials.

SUMMARY

In view of the problem of the prior art that overlapping between energy spectrum affects the capability of discriminating materials, there is provided a CT imaging system and a method.

According to an aspect of the invention, there is provided a CT imaging system comprising a X-ray source; a first detection and collection unit which is disposed to be opposite to the X-ray source and configured to perform a first CT scanning on an object to be detected to obtain scanning data; a reconstruction unit configured to reconstruct an image of a first resolution based on the scanning data; a second detection and collection unit which includes at least a photon counter detector and is configured to perform a second CT scanning on an area of interest in the image of the first resolution, the second CT scanning including scanning on the area of interest under a plurality of energy windows by the photon counter detector to obtain truncated energy spectrum data; wherein the reconstruction unit is further configured to supplement the truncated energy spectrum data by using the image of the first resolution as a priori image, and reconstruct an image of a second resolution from the supplemented energy spectrum data, the second resolution being higher than the first resolution.

According to another aspect of the invention, there is provided a CT imaging method comprising steps of performing a first CT scanning on an object to be detected, to obtain scanning data; reconstructing an image of a first resolution based on the scanning data; determining position information on an area of interest of the object to be detected from the reconstructed image; performing a second CT scanning on an area of interest in the image of the first resolution, the second CT scanning including at least scanning on the area of interest under a plurality of energy windows by a photon counter detector to obtain truncated energy spectrum data; supplementing the truncated energy spectrum data by using the image of the first resolution as a priori image; and reconstructing an image of a second resolution from the supplemented energy spectrum data, the second resolution being higher than the first resolution.

According to the embodiments of the invention, a CT local imaging can be achieved at a higher resolution. Compared with the conventional dual-energy CT system, the discrimination of energy spectrum is higher and the result so obtained is more stable by using a photon counter detector to collect photon count projection data of a plurality of energy windows and thus it may be decomposed into a plurality of basis functions.

BRIEF DESCRIPTION OF THE DRAWINGS

The implementations of the invention are illustrated in the drawings. The drawings and implementations provide some embodiments of the invention non-exclusively without limitation, where.

DETAILED DESCRIPTION OF THE EMBODIMENTS

Figure 1:
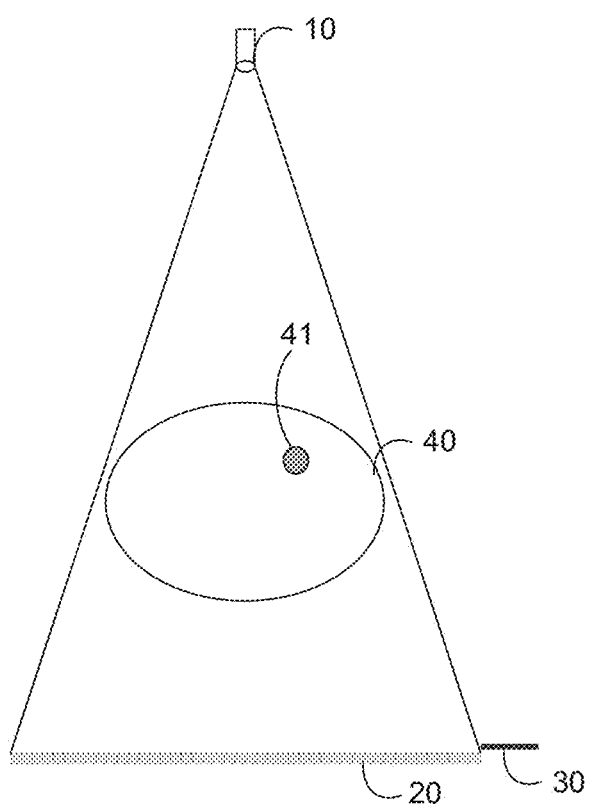
FIG. 1 illustrates a diagram of a first CT scanning process in a CT imaging system and a method according to an embodiment of the invention.

The particular embodiments of the invention are described below in details. It shall be noted that the embodiments herein are used for illustration only, but not limiting the invention. In the description below, a number of particular details are explained to provide a better understanding to the invention. However, it is apparent to those skilled in the art the invention can be implemented without these particular details. In other examples, well known circuits, materials or methods are not described so as not to obscure the invention.

Throughout the specification, the reference to "one embodiment," "an embodiment," "one example" or "an example" means that the specific features, structures or properties described in conjunction with the embodiment or example are included in at least one embodiment of the present invention. Therefore, the phrases "in one embodiment," "in an embodiment," "in one example" or "in an example" occurred at various positions throughout the specification may not refer to one and the same embodiment or example. Furthermore, specific features, structures or properties may be combined into one or several embodiments or examples in any appropriate ways. Moreover, it should be understood by those skilled in the art that the term "and/or" used herein means any and all combinations of one or more listed items.

In view of the problem of the prior art that overlapping between energy spectrum affects the capability of discriminating materials, there is provided a CT imaging system comprising a X-ray source; a first detection and collection unit which is disposed to be opposite to the X-ray source and configured to perform a first CT scanning on an object to be detected to obtain scanning data; a reconstruction unit configured to reconstruct an image of a first resolution based on the scanning data; a second detection and collection unit which includes at least a photon counter detector and is configured to perform a second CT scanning on an area of interest in the image of the first resolution, the second CT scanning including scanning on the area of interest under a plurality of energy windows by the photon counter detector to obtain truncated energy spectrum data; wherein the reconstruction unit is further configured to supplement the truncated energy spectrum data by using the image of the first resolution as a priori image, and reconstruct an image of a second resolution from the supplemented energy spectrum data, the second resolution being higher than the first resolution. In the solution, a photon counter detector is used to perform CT scanning on a local area of interest of the object to be detected, and thus the area of interest may be imaged under a plurality of energy windows.

According to an embodiment of the invention, the photon counter detector may use a semiconductor detector that has a high spatial resolution, a high energy resolution and a high temporal resolution, and may detect the energy of incident photons and count information under a certain condition. An energy spectrum imaging function may be achieved by using such a kind of detector in X-ray imaging. The photon counter detector mainly aims to detect energy of incident particles and count photons falling within an energy range based on predefined energy upper and lower limits. The collected result is a photon count in an energy window $[E_{min}, E_{max}]$. In performing imaging, the X-ray energy may be divided into a plurality of non-overlapping energy windows, within which the photons are counted to obtain data of a plurality of different energies. The current energy spectrum imaging techniques may be used for the following purposes: (1) when an energy window has a narrow width, it can be taken as a single-energy X-ray and attenuation coefficient information of a material under different energies may be obtained; (2) when an energy window has a wide width, it can be taken as a conventional dual-energy or multi-energy imaging to discriminate materials. Since the energy spectrum are not overlapped with each other, the basis function decomposition result is more stable; (3) the collected photon counts under different energy windows are weighted to obtain an image of an optimal contrast ratio and SNR.

The current photon counter detector has a detector of a size in the order of sub-millimeter, and is mainly used for Micro-CT. Regarding human body medical diagnose or security check, it is difficult to manufacture a photon counter detector that completely cover the scan field. In some diagnose application occasions, there may be cases that an imaging of a high resolution and a high contrast ratio is only needed for a local area of a small size, i.e., a local CT imaging is needed.

In view of the problem of the prior art, there is provided an X-ray energy spectrum CT local imaging system. The system adds a high-resolution photon counter detector to a conventional CT imaging system, and also a corresponding mechanical control mechanism and reconstruction algorithm software. For example, a large-size standard-resolution detector is a scintillator-type detector that performs common CT imaging. A small-size high-resolution photon counter detector performs energy spectrum CT imaging. The system may provide a higher spatial resolution, a better contrast ratio, more material information and thus is applicable in fields such as medical diagnose, industry detection and so on.

Figure 2:
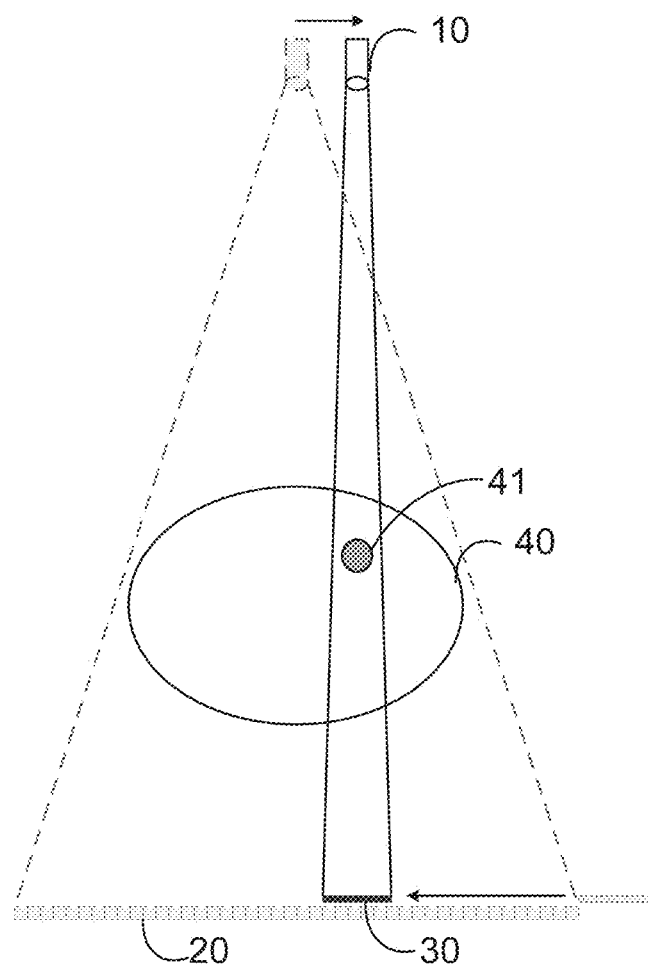
FIG. 2 illustrates a diagram of a second CT imaging process in a CT imaging system and a method according to an embodiment of the invention.

FIG. 1 illustrates a diagram of a first CT scanning process in a CT imaging system and a method according to an embodiment of the invention. FIG. 2 illustrates a diagram of a second CT imaging process in a CT imaging system and a method according to an embodiment of the invention.

As shown in FIG. 1, the CT imaging system according to the embodiment comprises a X-ray source 10, a first detection and collection unit 20 and a second detection and collection unit 30. The X-ray source 10, e.g., a X-ray machine, has a focus in the order of sub-millimeter. The first detection and collection unit 20 uses a conventional large field-of-view flat plane detector. The second detection and collection unit 30 uses for example a photon counter detector. As shown in FIG. 1, a common CT scanning is performed by moving the detector support (not shown) to have the area array detector align with an object to be detected 40. Then, a re-constructed image of a standard resolution is obtained by performing reconstruction with a cone beam FDK algorithm. Information on spatial position of an area of interest in the reconstructed image is determined. For example, the reconstructed image is displayed on a display. A user selects an area of interest via an input unit, and thereby information on spatial position of the area of interest is obtained. According to other embodiments, the area of interest may be determined by using an image processing algorithm. For example, an area whose gray level satisfies a condition in the reconstructed image is set as the area of interest.

After that, the X-ray source 10 and the photon counter detector in the second detection and collection unit are moved to be aligned with the area of interest 41. A local scanning for photon count under a plurality of (more than 2) energy windows is performed once with the area of interest 41 as the rotation center, as shown in FIG. 2. Data so obtained are energy spectrum data that are truncated at both sides. Then, the reconstructed image obtained by performing a common CT scanning is used as a priori image, and the truncated data are supplemented by means of a discrete projection approach. An appropriate smoothing process is also performed. An image of a high-resolution local energy spectrum attenuation coefficient is reconstructed from the supplemented energy spectrum data. Alternatively, in other embodiments, a basis-function decomposition post-processing may be performed on the image of attenuation coefficients under different energy windows to obtain decomposition coefficients, and thereby atomic numbers and an electron density map can be contained as following:

$$\mu_{E_1} = a_{E_1,1}\mu_1(E_1) + a_{E_1,2}\mu_2(E_1) + \ldots a_{E_1,N}\mu_N(E_1) \quad (1)$$

$$\ldots$$

$$\mu_{E_M} = a_{E_M,1}\mu_1(E_M) + a_{E_M,2}\mu_2(E_M) + \ldots a_{E_M,N}\mu_N(E_M)$$

wherein $\mu_{E_m}$ is the attenuation coefficient under the mth energy window, $a_{E_m,n}$ is the decomposition coefficient of the nth base material under the mth energy window, and $\mu_n(E_m)$ is the attenuation coefficient of the nth material under the mth energy window. The solution to the above equation (1) is the decomposition coefficients $a_{E_m,n}$ of the base materials. The atomic numbers and an electron density map of materials in the area of interest may be calculated thereby. Alternatively, in other embodiments, the reconstructed result obtained by performing a common CT scanning is used as a priori image, and the truncated data are supplemented by means of a discrete projection approach. An appropriate smoothing process is also performed. A reconstruction pre-processing is performed on the supplemented energy spectrum data. Since a photon counter detector is capable of collecting data of a number of energy windows at the same time, a number of basis functions, no more than the number of energy windows, are chosen in performing the basis function decomposition, and a combination of the basis functions, for example Compton effect, photoelectric effect, aluminum-based material, or carbon-based material, is used. In the case that the number of N energy windows is equal to the number of M basis functions, a non-linear multi-energy function is resolved:

$$p_i = \int_{E_{i,min}}^{E_{i,max}} S_i(E) e^{-\sum_{j=1}^{M} A_j f_j(E)} dE \quad (2)$$

$$i = 1, \ldots, N.$$

If the number of N energy windows is larger than the number of M basis functions, the following log-likelihood function may be constructed as following:

$$L(\vec{p} \mid \vec{A}) = \sum_{i=1}^{N} [\lambda_i(\vec{A}) + \ln p_i! - p_i \ln \lambda_i(\vec{A})] \quad (3)$$

$$\lambda_i(\vec{A}) = \overline{p}_i = \int_{E_{i,min}}^{E_{i,max}} S_i(E) e^{-\sum_{j=1}^{M} A_j f_j(E)} dE$$

$$i = 1, \ldots, N,$$

wherein $E_{i,max}$ and $E_{i,min}$ are the upper limit and the lower limit of the ith energy window, respectively, $p_i$ is the photon count collected under the ith energy window by the detector, $p_i!$ is the factorial of $p_i$, $\lambda_i$ is the expectation of $p_i$, $A_j$ is the line integral of coefficients of the jth basis function, $f_j(E)$ is the jth basis function, and $S_i(E)$ is the energy spectrum of the ith energy window. Minimizing the objective function $L(\overline{p}|\overline{A})$ will result in a line integral $\overline{A}$ of decomposition coefficients of respective basis functions. A common reconstruction algorithm, e.g., FBP algorithm, may be used to obtain a decomposition coefficient map. The photoelectric effect and Compton effect may be used to calculate the atomic number and the electron density of a material. The coefficient of a base material indicates the mass density of the material in the object.

Figure 3:
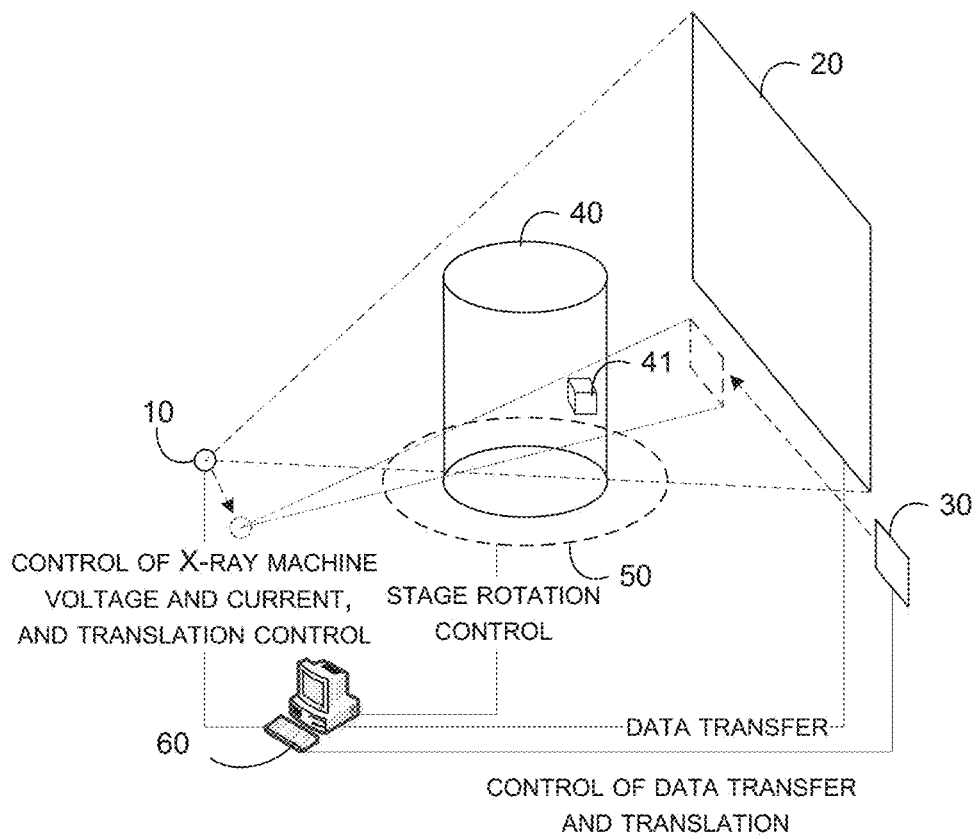
FIG. 3 illustrates a schematic diagram of a CT imaging system according to an embodiment of the invention.

FIG. 3 illustrates a schematic diagram of a CT imaging system according to an embodiment of the invention. The CT imaging system according to the embodiment comprises a X-ray source 10, a mechanical movement mechanism and controller, a detector and a data collection system.

The X-ray source 10, such as an X-ray machine, may select a proper X-ray machine focus size according to the resolution of imaging, for example, a micro-focus of a size in the order of sub-millimeter, so as to obtain a high resolution image. The mechanical movement mechanism and collector comprises a stage 50, a housing of the X-ray machine and the detector, and a control system. The stage 50 may adjust the position of the rotation center by translation. The housing may align the X-ray machine and detectors 20 and 30 with the rotation center by translation. In the embodiment, a circular scanning where the stage rotates while the housing is stationary is described. Since the stage and the housing move in a relative motion, it is certain that the method according to the embodiment is applicable in the case that the stage is stationary while the housing rotates.

The detector and data collection system 20 and 30 comprise an area array X-ray detector 20 which covers completely the object to be scanned and a photon counter detector 30 which has a smaller field of view and a high resolution. The two detectors are fixed on respective detector stands. One of the two detectors is chosen to perform imaging by translating the stands. The data collection system comprises a reading circuit, a collection triggering circuit, a data transmission circuit, and so on.

The reconstruction unit 60 is for example a master control and data processing computer, responsible for control during the time the CT system is running, comprising mechanical movement, electrical control, safety interlocking control, image construction, and the like.

According to some embodiments, the system further comprises a display connected to the reconstruction unit 60 and configured to display a high resolution image by superposing it on at least part of the common CT image and highlight the high resolution image by for example framing the high resolution image. Alternatively, the reconstruction unit 60 may mix the common CT image and the high resolution image, and display the mixed image on the display.

Figure 4:
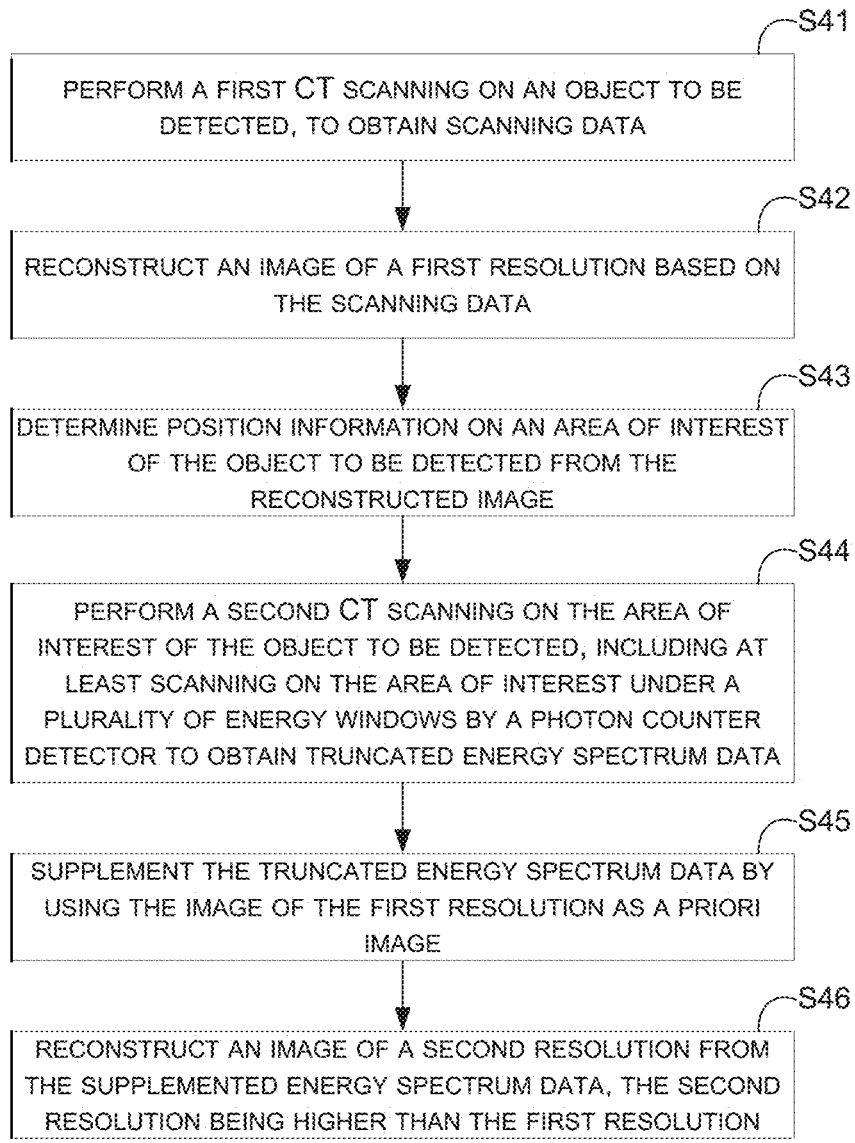
FIG. 4 illustrates a flowchart of a CT imaging method according to an embodiment of the invention.

FIG. 4 illustrates a flowchart of a CT imaging method according to an embodiment of the invention. As shown, a first CT scanning is performed on an object to be detected at step S41 to obtain scanning data. For example, the first detection and collection system and X-ray source in the system shown in FIG. 3 may be used to perform CT scanning on the object 40 to be detected. After that, an image of a first resolution is reconstructed from the scanning data at step S42.

At step S43, position information on an area of interest of the object is determined from the reconstructed image. For example, the reconstructed image is displayed on a display connected to the reconstruction unit. A user selects an area of interest 41. As an alternative, the area of interest may be determined by using an image processing algorithm to analyze the reconstructed image. For example, an area whose gray level satisfies a condition in the reconstructed image is set as the area of interest.

At step S44, a second CT scanning is performed on the area of interest of the object. The second CT scanning comprises at least scanning the area of interest under a plurality of energy windows by a photon counter detector to obtain truncated energy spectrum data. For example, in the system shown in FIG. 3, the X-ray source 10 and the second detection and collection unit 30 are moved to perform CT scanning under a plurality of energy windows on the area of interest 41.

At step S45, the truncated data are supplemented by using the image of the first resolution as a priori image. An image of a second resolution higher than the first resolution is reconstructed from the supplemented energy spectrum data at step S46. For example, an image of a higher resolution is reconstructed by means of the foregoing pre-processing or the post-processing.

According to some embodiments, the system further comprises a display connected to the reconstruction unit 60 and configured to display a high resolution image by superposing it on at least part of the common CT image and highlight the high resolution image by for example framing the high resolution image. Alternatively, the reconstruction unit 60 may mix the common CT image and the high resolution image, and display the mixed image on the display.

According to the embodiment, there is a provided a CT imaging system comprising both a common energy deposition detector and a high resolution photon counter detector, and a data processing and image reconstruction method thereof. The system may provide a common CT image, a local high resolution CT image and a local energy spectrum CT image, and is applicable to various fields, for example non-destructive detection, medical diagnose and others.

The foregoing detailed description has set forth various embodiments of the CT imaging system and method of the same via the use of block diagrams, flowcharts, and/or examples. Insofar as such block diagrams, flowcharts, and/or examples contain one or more functions and/or operations, it will be understood by those skilled in the art that each function and/or operation within such examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of those skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present invention has been described with reference to several typical embodiments, it is apparent to those skilled in the art that the terms are used for illustration and explanation purpose and not for limitation. The present invention may be practiced in various forms without departing from the esprit or essence of the invention. It should be understood that the embodiments are not limited to any of the foregoing details, and shall be interpreted broadly within the esprit and scope as defined by the following claims. Therefore, Modifications and alternatives falling within the scope of the claims and equivalents thereof are to be encompassed by the scope of the present invention which is defined by the claims as attached.

What is claimed is:

1. CT imaging system comprising
a X-ray source;
a first detection and collection unit which is disposed to be opposite to the X-ray source and configured to perform a first CT scanning on an object to be detected to obtain scanning data;
a reconstruction unit configured to reconstruct an image of a first resolution based on the scanning data;
a second detection and collection unit which includes at least a photon counter detector and is configured to perform a second CT scanning on an area of interest in the image of the first resolution, the second CT scanning including scanning on the area of interest under a plurality of energy windows by the photon counter detector to obtain truncated energy spectrum data;
wherein the reconstruction unit is further configured to supplement the truncated energy spectrum data by using the image of the first resolution as a priori image, and to reconstruct an image of a second resolution from the supplemented energy spectrum data, the second resolution being higher than the first resolution.

2. The CT imaging system according to claim 1, wherein the X-ray source is a X-ray machine whose focus has a size in the order of sub-millimeter.

3. The CT imaging system according to claim 1, wherein the first detection and collection unit comprises an area array X-ray detector.

4. The CT imaging system according to claim 1, wherein the second detection and collection unit is further configured to reconstruct an image of attenuation coefficients under the plurality of energy windows at the second resolution.

5. The CT imaging system according to claim 4, wherein a basis-function decomposition post-processing is performed on the image of attenuation coefficients under the plurality of energy windows to obtain decomposition coefficients under different effects, and atomic numbers and an electron density map of the area of interest are calculated thereby.

6. The CT imaging system according to claim 4, wherein the reconstruction unit is further configured to perform basis function decomposition pre-processing on each of the plurality of energy windows to obtain line integrals of decomposition coefficients of respective basis functions, reconstruct decomposition coefficients of respective basis functions, and calculate atomic numbers and electron density of materials in the area of interest based on the decomposition coefficients of respective basis functions.

7. The CT imaging system according to claim 6, wherein the reconstruction unit is further configured to solve a non-linear multi-energy equation to obtain the line integrals of decomposition coefficients of basis functions and thereby to reconstruct a decomposition coefficient map if the number of energy windows is equal to the number of basis functions.

8. The CT imaging system according to claim 6, wherein the reconstruction unit is further configured to obtain line integrals of decomposition coefficients of basis functions by constructing a log-likelihood function and thereby to reconstruct a decomposition coefficient map if the number of energy windows is larger than the number of basis functions.

9. The CT imaging system according to claim 1, further comprising a display connected to the reconstruction unit and configured to display the image of the second resolution by superposing it on at least part of the image of the first resolution and highlight the image of the second resolution.

10. The CT imaging system according to claim 1, wherein the reconstruction unit is further configured to determine the area of interest by using an image processing algorithm to process the image of the first resolution.

11. The CT imaging system according to claim 1, further comprising:
   a display connected to the reconstruction unit and configured to display the image of the first resolution, and
   an input unit configured to receive a selection of a specific area in the image of the first resolution from a user as the area of interest.

12. The CT imaging system according to claim 11, wherein the reconstruction unit is further configured to mix the image of the first resolution and the image of the second resolution, and display the mixed image on the display.

13. A CT imaging method comprising:
   performing a first CT scanning on an object to be detected, to obtain scanning data;
   reconstructing an image of a first resolution based on the scanning data;
   determining position information on an area of interest of the object to be detected from the reconstructed image;
   performing a second CT scanning on the area of interest of the object to be detected, the second CT scanning including at least scanning on the area of interest under a plurality of energy windows by a photon counter detector to obtain truncated energy spectrum data;
   supplementing the truncated energy spectrum data by using the image of the first resolution as a priori image; and
   reconstructing an image of a second resolution from the supplemented energy spectrum data, the second resolution being higher than the first resolution.

14. The CT imaging method according to claim 13, wherein reconstructing an image of a second resolution higher than the first resolution from the supplemented energy spectrum data comprises reconstructing an image of attenuation coefficients under the plurality of energy windows at the second resolution.

15. The CT imaging method according to claim 14, wherein reconstructing an image of a second resolution higher than the first resolution from the supplemented energy spectrum data further comprises performing a basis-function decomposition post-processing on the image of attenuation coefficients under the plurality of energy windows to obtain decomposition coefficients under different effects, and calculating atomic numbers and an electron density map of the area of interest thereby.

16. The CT imaging method according to claim 13, wherein reconstructing an image of a second resolution higher than the first resolution from the supplemented energy spectrum data comprises performing basis function decomposition on each of the plurality of energy windows to obtain line integrals of decomposition coefficients of respective basis functions, reconstructing decomposition coefficients of respective basis functions, and calculating atomic numbers and electron density of materials in the area of interest based on the decomposition coefficients of respective basis functions.

17. The CT imaging method according to claim 16, wherein if the number of energy windows is equal to the number of basis functions, the line integrals of decomposition coefficients of basis functions are obtained by solving a non-linear multi-energy equation, and a decomposition coefficient map is reconstructed.

18. The CT imaging method according to claim 16, wherein if the number of energy windows is larger than the number of basis functions, the line integrals of decomposition coefficients of basis functions are obtained by constructing a log-likelihood function, and a decomposition coefficient map is reconstructed.

* * * * *